United States Patent [19]

Barnett et al.

[11] Patent Number: 5,593,847
[45] Date of Patent: Jan. 14, 1997

[54] MONITORING OF NC 50/90 IN BLOOD SAMPLES OF BREAST CANCER PATIENTS

[75] Inventors: Thomas R. Barnett, Prospect; James J. Elting, Madison, both of Conn.; William J. Allard, Poughquag, N.Y.

[73] Assignee: Bayer Corporation, Tarrytown, N.Y.

[21] Appl. No.: 170,141

[22] Filed: Dec. 20, 1993

Related U.S. Application Data

[63] Continuation-in-part of Ser. No. 35,125, Mar. 19, 1993, abandoned, which is a continuation of Ser. No. 815,934, Dec. 30, 1991, abandoned.

[51] Int. Cl.$^6$ .................. G01N 33/574; G01N 33/53; C07K 16/00; C12P 21/08
[52] U.S. Cl. ............... 435/7.23; 530/388.8; 435/810; 435/975; 436/64; 436/813
[58] Field of Search ................ 435/7.23, 7.21, 435/7.9, 7.92, 7.94; 530/388.85, 387.7, 388.8; 436/518, 64, 813

[56] References Cited

PUBLICATIONS

Chavenel et al, Oncodev. Biol. and Med. 4:209–217 (1983).
Yeung et al, Tumor Biol. 9:119 (1992).
von Kleist et al, Br. J. Cancer 35:875–880 (1977).
Wahren et al, Int. J. Cancer 29:133–137 (1982).
Harlozinska et al, Eur. J. Surg. Oncol.17:59–64 (1991).
Reck et al, Tumor Biol.13:110–111 (1992).
Radosevich et al., Tumor Biol., vol. 10, pp. 281–288, 1989.
Barnett et al., Genomics, vol. 3, pp. 59–66, 1988.
Suzuki et al., Cancer Res., vol. 47, No. 18, pp. 4782–4787, 1987 (abstract only).

Primary Examiner—Toni R. Scheiner
Assistant Examiner—Yvonne Eyler
Attorney, Agent, or Firm—Andrew L. Klawitter

[57] ABSTRACT

A method for aiding in the diagnosis of, and monitoring the progression of, breast cancer in a patient by measuring the amount of NCA 50/90 in a blood sample, e.g. serum sample, obtained from the patient. Measurement in a single sample of an amount of NCA 50/90 significantly higher than the mean amount of NCA 50/90 in the normal population is an indication of breast cancer in the patient. The progression of breast cancer can also be monitored by performing a series of specific immunoassays over time to determine changes in the level of NCA 50/90 in blood samples. Increases in blood NCA 50/90 levels over time are indicative of a deteriorating condition whereas decreasing levels of blood NCA 50/90 over time indicate an improving condition.

14 Claims, 15 Drawing Sheets

MONITORING OF NC 50/90 IN BLOOD SAMPLES OF BREAST CANCER PATIENTS

CROSS-REFERENCE TO RELATED APPLICATION

This is a continuation-in-part of application Ser. No. 035,125, filed Mar. 19, 1993, which is a continuation of application Ser. No. 815,934, filed Dec. 30, 1991, now abandoned.

BACKGROUND OF THE INVENTION

The present invention relates to monitoring the progression or stage of disease in breast cancer patients. More particularly, the invention relates to such monitoring methods based on measurement of cancer marker blood levels.

A number of substances have been determined to be useful markers in monitoring the course of various cancer types. Some useful markers that have been identified are oncofetal antigens such as carcinoembryonic antigen (CEA) and alpha-fetoprotein, tissue-specific antigens such as prostate-specific antigen (PSA), and mucin antigens such as those conventionally known as CA-125 and CA-19-9. Immunoassays for antigens such as these are typically used as confirmatory tests at the time of diagnosis and subsequently for monitoring patient status. Occasionally, the use of such tests crosses the boundaries of tumor type (for example, the use of CEA tests in colon, breast, and lung cancer, and alpha-fetoprotein in hepatocellular and testicular cancer), but the utility of each test type is foremost for a single tumor type (for example, PSA for prostate cancer and CA-125 for ovarian cancer).

A family of antigenic proteins have been identified which are genetically and immunologically related to CEA (Thompson, J. and W. Zimmerman (1988) Tumor Biol. 9, 63–83; and Barnett, T. and W. Zimmerman (1990) Tumor Biol. 11, 59–63). Among these are the nonspecific cross-reacting antigens (NCAs), the trans-membrane antigens designated biliary glycoprotein (BGP, and sometimes referred to as TM-CEAs), and the family of pregnancy-specific β-glycoproteins (PSGs) (for a description of the accepted nomenclature of these genes and their protein products, reference can be made to: Barnett, T. and W. Zimmerman (1990) Tumor Biol. 11, 59–63). Molecular cloning of the CEA gene family has enabled the identification of 22 members, of which 20 are probably expressed (Frangsmyr, L. et al. (1992) Tumor Biol. 13, 98–99; and Hammerstrom, S. et al Tumor Biol. 13, 57). The results of molecular genetic analysis have given a better understanding of the complex group of glycoproteins in the CEA gene family.

NCA was originally described as a component of normal tissue which cross-reacted with antibodies raised to CEA (Mach, J.-P. and G. Pusztaszeri (1972) Immunochemistry 9, 1031–1034; and von Kleist, S., Chavenel, G. and P. Burtin (1972) Proc. Natl. Acad. Sci. USA 69, 2492–2494). As such, NCA was considered a potential nontumor derived interferant in assays for CEA. Molecular cloning identified one species of NCA of calculated $M_r$ 37,000 designated by one group as NCA-BT (Barnett, T., Goebel, S. J., Nothdurft, M. A. and J. J. Elting (1988) Genomics 3, 59–66) to denote the breast tissue origin of the cloned cDNA, and by others as NCA (Tawaraji, Y. et al. (1988) Biochem. Biophys. Res. Commun. 150, 89–96; and Neumaier, M. et al (1988) J. Biol. Chem. 263, 3203–3207). This single NCA species has since been termed NCA 50/90 (Kolbinger, F., Schwarz, K., Brombacher, F., von Kleist, S., and Grunert, F. (1989) Biochem. Biophys. Res. Commun. 161, 1126–1134) because it was now known to be processed into two mature isoforms of $M_r$ 50,000 and $M_r$ 90,000 which have different degrees of glycosylation. A second and distinct NCA gene was subsequently identified by molecular cloning from leukemic cells that codes for an $M_r$ 95,000 glycoprotein (Kuroki, M. et al (1991) J. Biol. Chem. 266, 11810–11817). This latter NCA has been termed NCA 95.

Early studies also identified a cross-reacting antigen from adult stools and from meconium which, for historical reasons, was termed NCA-2 (Burtin, P., Chavenel, G. and H. Hirsch-Marie (1973) J. Immunol. 111, 1926–1928). The designation of this antigen as NCA is, however, a misnomer. It has been identified as a proteolytic fragment of CEA since the first 30 amino acids of the meconium-derived NCA-2 are identical in sequence with CEA (Siepen, D. et al (1987) Biochem. Biophys. Res. Commun. 174, 212–218). In contrast, cDNAs for NCA 50/90 and NCA 95 have been described and code for distinct and different amino acid sequences in this region. Indeed, a recent report suggests that variability in CEA results obtained with different commercial kits may be due to interference with NCA-2 (O. P. Bormer (1991) Clin. Chem. 37, 1736–1739).

Given the improved understanding of the CEA gene family resulting from molecular cloning analysis, monoclonal antibodies can now be identified which recognize specific family members and do not cross react with closely related molecules. Previous attempts to raise antibodies to NCA have been plagued with the problem of cross reactivity with CEA family members. This may explain why NCA has been considered a poor serum marker for cancer diagnosis and monitoring (Shively, J. E., Spayth, V., Chang, F.-F., Metter, G. E., Klein, L., Present, C. A., and C. W. Todd (1982) Cancer Res. 42, 2502–2513; and Burtin, P., Chavenel, G., Hendrick, J. C. and N. Frenoy (1986) J. Immunol. 137, 839–845). It has been further speculated that NCA-specific monoclonal antibodies such as are now widely accepted for CEA and other antigens would be very difficult to develop (Burtin, P. et al., supra).

In addition, it is now clear that members of the CEA gene family are differentially expressed by various tumor types. For example, it is well known that CEA is expressed in most if not all colorectal carcinomas, while expression is limited to a minority of breast carcinomas. Prior to the generation of specific monoclonal antibodies, attempts to quantitate NCA levels in the serum of cancer patients were confounded by the presence of other CEA gene family members that cross reacted with the antibodies being used. However, because of the successful production of monoclonal antibodies specific to NCA 50/90, it is now possible to determine the incidence of elevated NCA 50/90 protein in different cancer types.

Although there have been reports of monoclonal antibodies specific for NCA 50/90 (Chavenel, G., Frenoy, N., Escribano, M. J. and P. Burtin (1983) Oncodev. Biol. and Med. 4, 209–217; and Yeung, M., M.-W. Hammerstrom, M. L., Baranov, V. and S. Hammerstrom (1992) Tumor Biol. 9, 119), there have been no reports of a monoclonal antibody which binds to NCA 50/90 but does not recognize any other CEA family members including CEA, NCA 95, NCA 2, BGP or PSG. Similarly, several reports have suggested that NCA may be elevated in the serum of cancer patients (von Kleist, S., Troupel, S., King, M. and P. Burtin (1977) Br. J. Cancer 35, 875–880; and Wahren, B., Gahrton, G., Ruden, U. and S. Hammerstrom (1982) Int. J. Cancer 29, 133–1.37; and Harlozinska, A., Rachel, F., Gawlikowski, W., Richter, R. and J. Kolodziej (1991) Eur. J. Surg. Oncol. 17, 59–64;

and Reck:, W., Daniel, S., Nagel, G., Hirn, M., von Kleist, S., and F. Grunert (1992) Tumor Biol. 13, 110–111), but these measurements utilized antibodies that have not been shown to recognize NCA 50/90 to the exclusion of other CEA-related molecules. In addition, there have been no reports of a correlation between blood NCA levels and the clinical status of any particular cancer patients.

Previous attempts to quantitate the level of NCA 50/90 in the serum have been hampered by the lack of a suitable standard. Measurements of NCA in blood have shown mean values in serum from normal individuals of from 30 ng/ml (Harlozinska, A., et al. supra) to 130 ng/ml (von Kleist, S., Troupel, S., King, M. and P. Burtin (1977) Br. J. Cancer 35, 875–880). This is due to the use of biochemically purified NCA as a standard to calibrate immunoassay measurements of NCA in blood and blood fluids. Just as the monoclonal antibodies have not been demonstrated to specifically recognize NCA 50/90, neither has the purity of the NCA standard preparations been determined.

SUMMARY OF THE INVENTION

It has now been found that NCA 50/90 can be significantly elevated in the blood of patients with breast cancer. Accordingly, the present invention provides a method for aiding in the diagnosis of breast cancer in a patient, comprising the steps of determining the amount of NCA 50/90 in a blood sample obtained from said patient, and comparing such measured amount of NCA 50/90 to the mean amount of NCA 50/90 in the normal population, whereby the presence of a significantly increased higher amount of NCA 50/90 in the patient's blood is an indication of breast cancer in the patient. The present method also provides a means for monitoring the progression of the disease. Increases in blood NCA 50/90 levels measured by performing a series of specific immunoassays over time indicate a deteriorating condition in a significant number of patients while decreases in blood NCA 50/90 levels indicate an improving condition in such patients.

DESCRIPTION OF THE PREFERRED EMBODIMENTS

Figure 1:
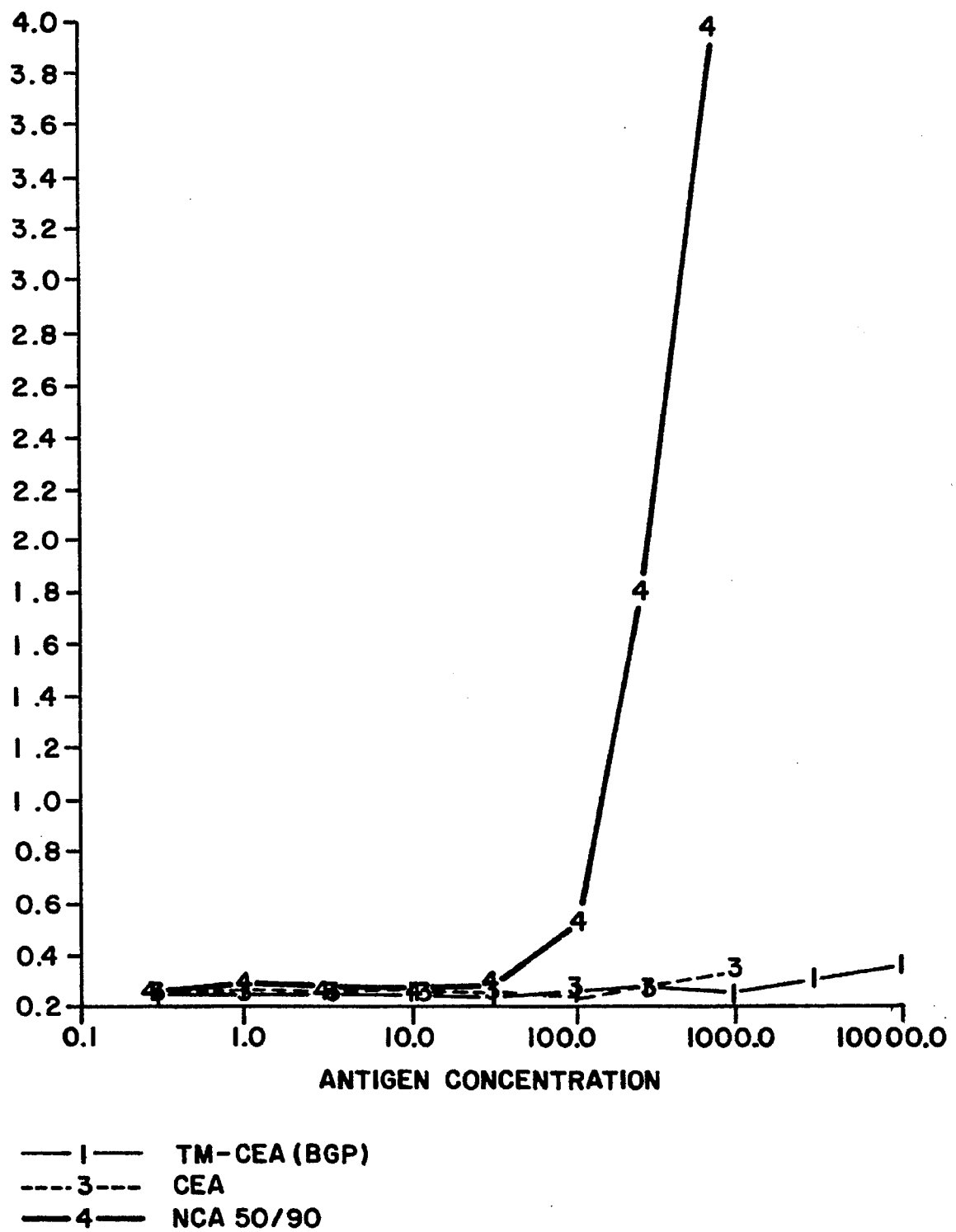
FIG. 1 is a graph showing the specificity of the particular immunoassay described in the Examples below for NCA 50/90 compared to CEA and BGP.

Essentially any method may be employed in the measurement of blood (e.g., serum or plasma) NCA 50/90 levels. Typically, such measurement will be performed by sandwich immunoassay using two antibody reagents, one of which is specific for NCA 50/90 (showing no substantial reactivity with other CEA family member antigens, particularly CEA, NCA 95 and BGP), while the second antibody can bind specifically to NCA 50/90 or can be raised against a different immunogen but crossreacts with NCA 50/90. Assay format and methods for the preparation of the required antibody reagents can be selected by the skilled worker in the field. Suitable antibody reagents can be labeled, e.g., enzymelabeled, or immobilized, e.g., coated onto a microtiter plate, bound to plastic or magnetic beads or particles, and can be comprised of whole immunoglobulins, e.g., IgG or IgM, or fragments, e.g., Fab, Fab', and F(ab')$_2$ fragments, or aggregates thereof.

Preferably, the NCA 50/90 specific antibody reagent is prepared by immunization of a host animal with a suitable immunogen such as an NCA 50/90 containing immunogen mixture, e.g., a purified extract of spleen or tumor cells; NCA 50/90-expressing transfectant cell lines (see European Patent Publication 346,702); an immunogen conjugate comprising a synthetically prepared peptide coupled to a conventional immunogenic carrier molecule, where the peptide has an amino acid sequence encompassing an epitope of NCA 50/90; and the like as will be understood in the art.

Antibody reagents comprising monoclonal antibodies will be generally preferred. Particularly preferred NCA 50/90 specific monoclonal antibodies are those which bind to substantially the same epitope as that produced by the hybridoma that was deposited on Nov. 18, 1992, with the American Type Culture Collection, 12301 Parklawn Drive, Rockville, Md. 20852 and which has been given deposit accession number ATCC HB 11204.

It will be understood that a number of standard methods can be used in order to determine whether a particular monoclonal antibody binds to substantially the same epitope as the above-mentioned antibody whose hybridoma has been deposited with the ATCC. A particularly useful method is competitive binding, wherein the ability of the antibody of interest to bind to NCA 50/90 in the presence of the reference antibody is measured. Substantial inability of both antibodies to bind simultaneously indicates that substantially the same epitope is involved.

It will be understood that, similar to other types of accepted disease monitoring methods, the present method will not be useful on every patient diagnosed with breast cancer. Rather, the physician will use NCA 50/90 blood values in combination with other diagnostic values and clinical observations to diagnose the onset of breast cancer, thereby providing a method for screening a select population for the disease, and further, to develop a course of treatment and therapy for each individual patient. It is also contemplated that monitoring blood levels of NCA 50/90 will provide a means for monitoring the progress of a cause of therapy for an individual patient.

The present invention will now be illustrated, but is not intended to be limited by, the following examples.

EXAMPLES

Study 1

Mab 228.2—BALB/C mice were immunized with 50 µg of an emulsion of NCA purified from human spleen (von Kleist, S. and P. Burtin (1969) Cancer Res. 29:1961–1964), and Freund's complete adjuvant. Spleens from hyperimmune animals were removed from euthanized animals and the splenocytes were fused with AG8 mouse myeloma cells (ATCC CRL 1580). The resulting hybridomas were screened for anti-NCA antibody production by sandwich ELISA. Positive clones were subsequently screened for anti-CEA and anti-BGP (TM-CEA) activity (see Barnett, T. and W. Zimmerman supra; and see Barnett, T. R., Kretschmer, A., Austen, D.A., Goebel, S. J., Hart, J. T., Elting, J. J., and M. E. Kamarck (1989) J. Cell Biol. 108:267–276) by sandwich ELISA assay. Those clones specific for NCA 50/90 were recloned and rechecked for cross reactivity with CEA and BGP (TM-CEA) by ELISA and again by FACS analysis using recombinant mouse cell lines expressing CEA, NCA 50/90 or BGP on their plasma membranes (see European Patent Publication No. 346,702). The result of this screening process was identification of Mab 228.2 (deposited with the ATCC, supra) which is specific for NCA 50/90 with no detectable reactivity with CEA, NCA 95 or BGP by ELISA.

Mab 176.7.5—BALB/C mice were immunized with BGP as described in U.S. patent application Ser. No. 480,428, filed Feb. 15, 1990. The hybridoma that produces the selected antibody has been deposited with the American Type Culture Collection, Rockville, Maryland, USA, and given the designation ATCC HB-10411. This antibody reacts with both NCA 50/90 and BGP but not with CEA. This antibody was crosslinked to calf intestine alkaline phosphatase (Biozyme Corp., San Diego, Calif., USA) after thiolation of the antibody with 2-iminothiolane using the heterobifunctional cross-linking reagent sulfo-SMPB (Pierce Chem. Co., Rockford, Ill., USA). This conjugate is hereafter designated 176.7.5-A.P.

NCA Calibrator—NCA purified from human spleen (von Kleist, S. et al, supra) was used as the calibrator for the NCA 50/90 assay. The amount of antigen was determined by amino acid analysis of a hydrolyzed sample of the purified NCA. Assay calibrators were made by diluting purified NCA into PBST-BSA (see below).

NCA-Specific Immunoassay—A sandwich ELISA was configured using NCA-specific Mab 228.2 as the solid phase capture antibody and Mab 176.7.5-A.P. as the reporter antibody. Mab 228.2 was coated in 100 µl of 0.1M $Na_2CO_3$/$NaHCO_3$, pH 9.0, onto the wells of microtiter ELISA plates (product ID#25801, Corning Glass Works, Corning, N.Y., USA) for 1 hour at 37° C. The wells were blocked with 300 µl 0.1% Tween-20 (polyoxyethylenesorbitan monolaureate) in 0.05M Na phosphate buffer, pH 7.2, 0.1M NaCl and 0.01% Thimerosal (PBST) for 1 hour at 37° C. After washing the plate 5 times with PBST, 50 µl of antigen solution [calibrators in PBST with 5% bovine serum albumin (PBST-BSA) or serum unknowns] were added and incubated for 2 hours at 37° C. After washing 5 times with PBST, 100 µl of 176.7.5-A.P. (15 µg/ml in PBST) was added to each well and incubated for 1 hour at 37° C. After washing, 200 µl of p-nitrophenyl phosphate (in 1.0M diethylamine buffer, pH 9.8) was added to each well and incubated for 30 minutes at room temperature. Absorbance at 405 nm was then determined and the amount of antigen in the test serum samples was determined from the calibrator standard curve.

Patient serum samples—Serum samples from clinically confirmed breast cancer patients were obtained from the University of Texas M.D. Anderson Cancer Center, Houston, Tex., USA. Samples from clinically normal individuals were obtained from M.D. Anderson and from in-house volunteers.

Results

Figure 2:
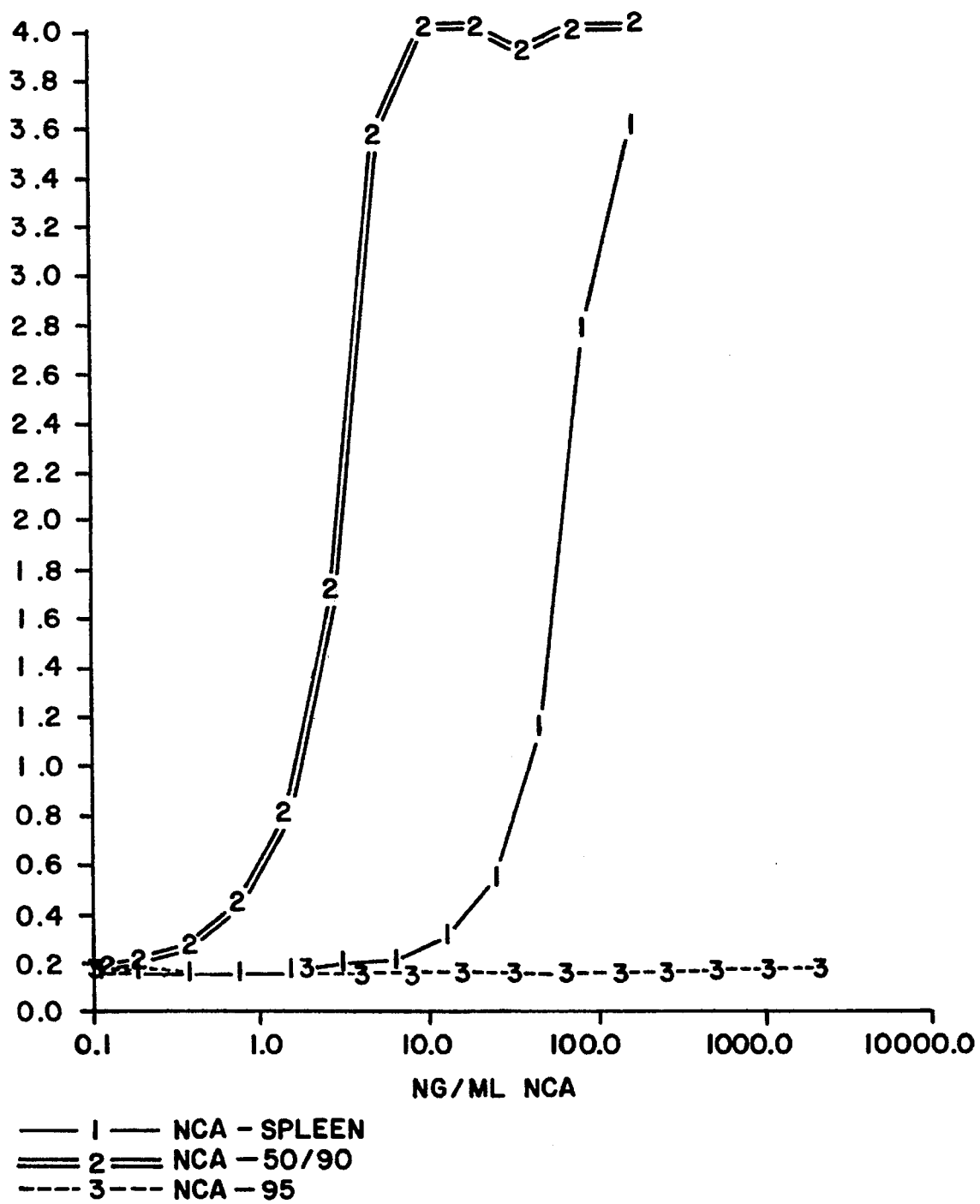
FIG. 2 is a graph showing the specificity of the particular immunoassay described in the Examples below for NCA 50/90 compared to recombinant NCA 95 and NCA purified from the spleen which was shown by amino acid sequencing to be identical to NCA 50/90.
Figure 3:
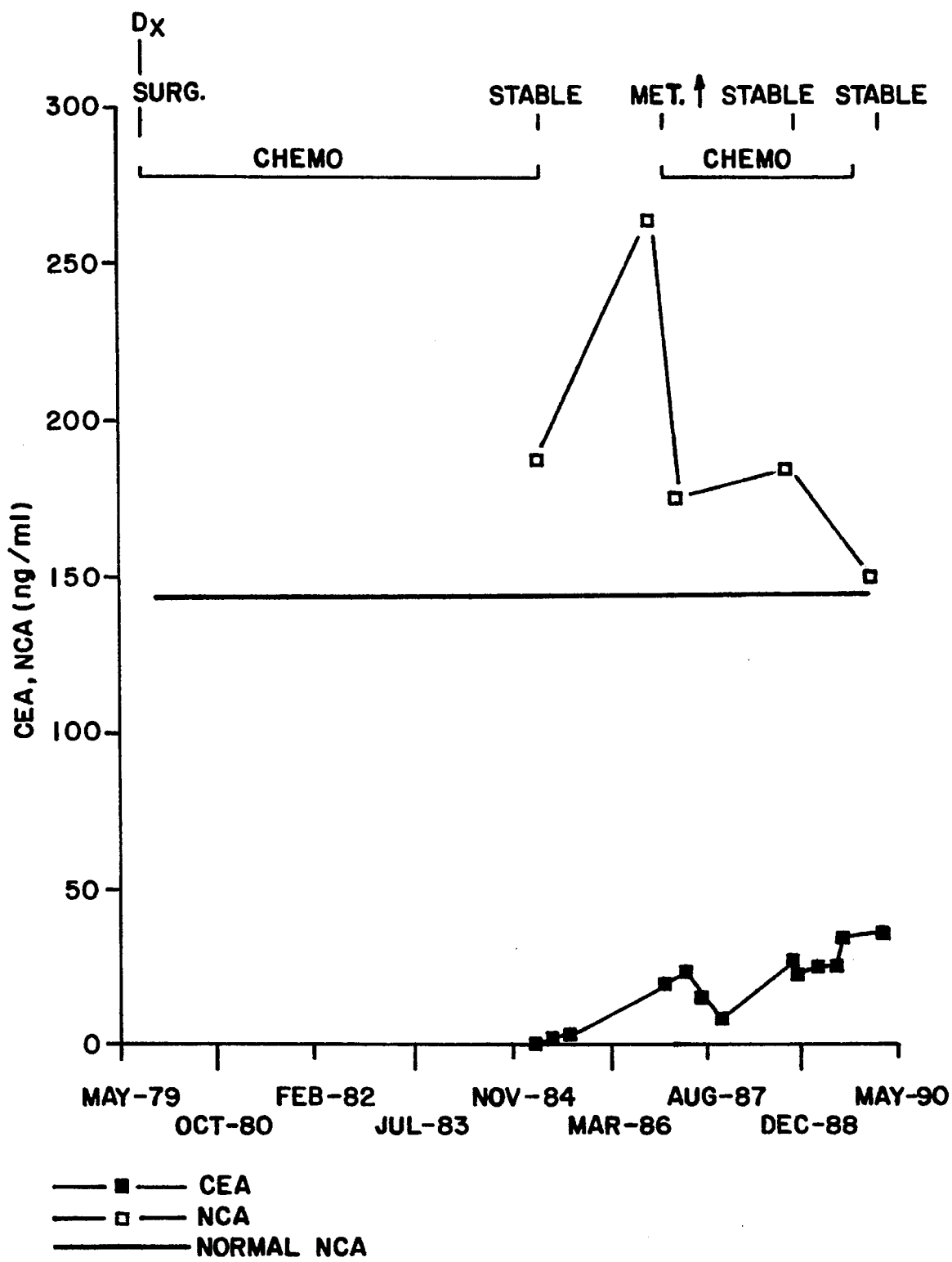
FIGS. 3–8 are graphs showing a comparison of the correlations of NCA 50/90 and CEA blood levels with the stage of breast cancer in patients under treatment.
Figure 4:
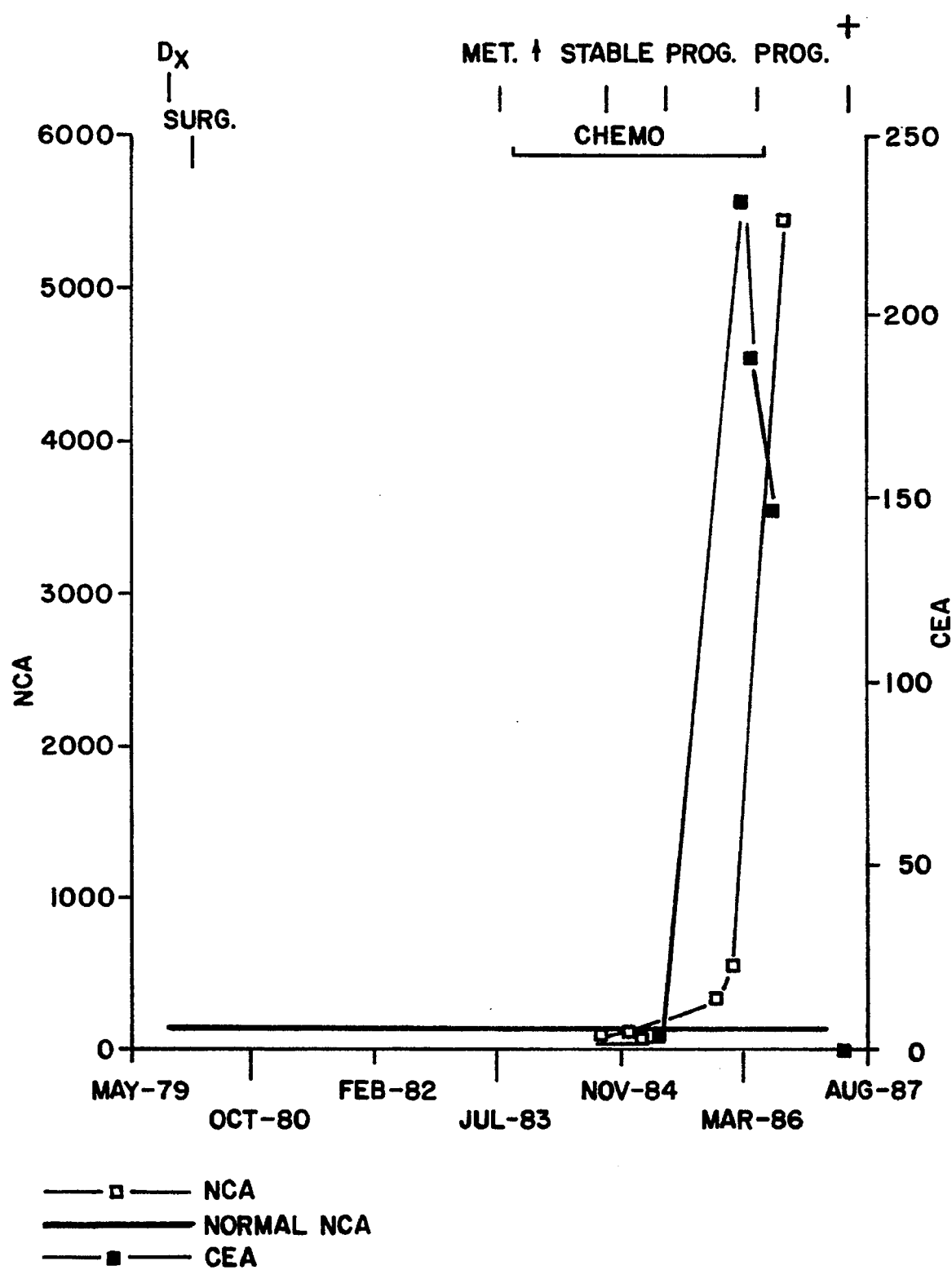
Figure 5:
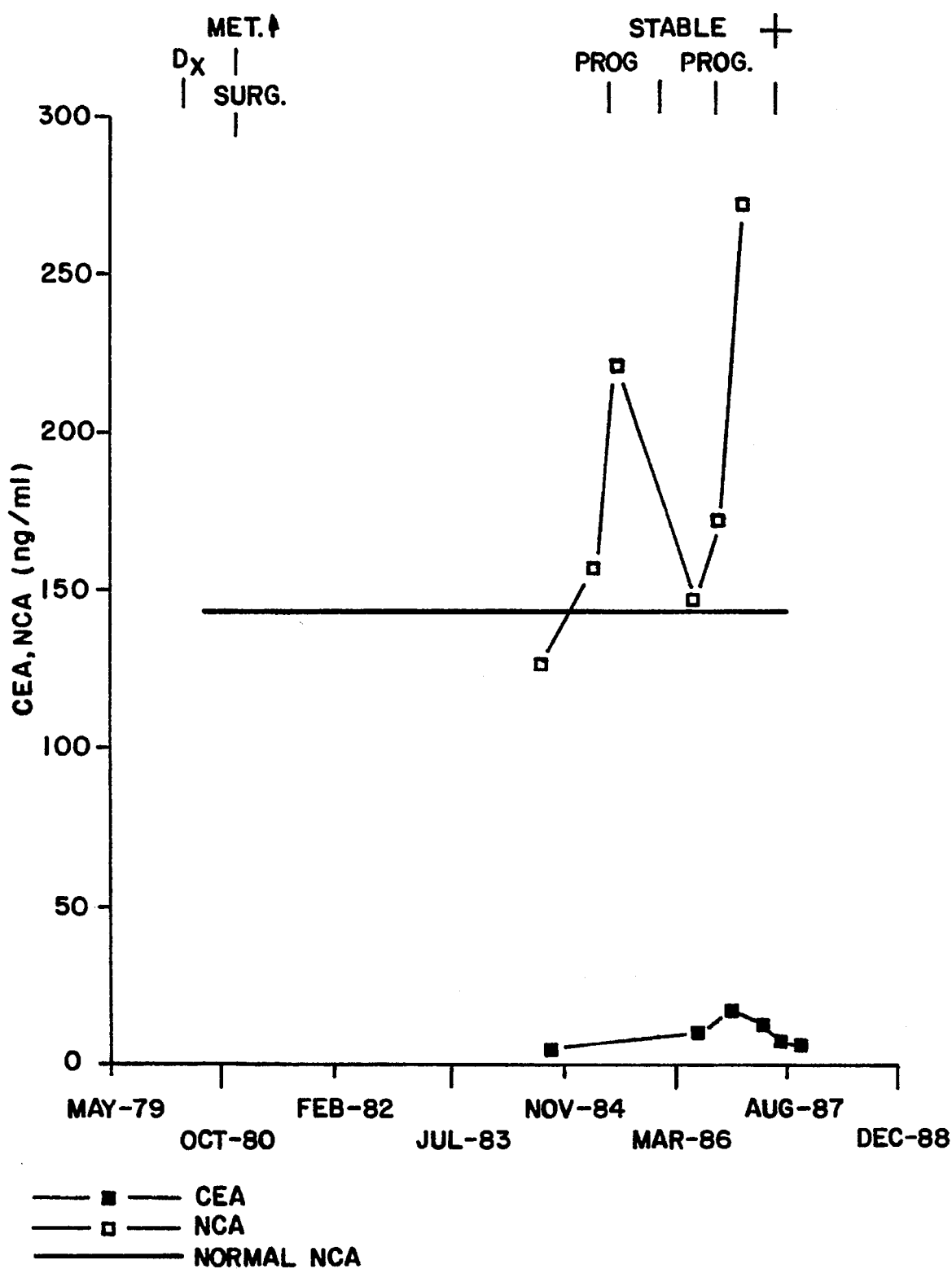
Figure 6:
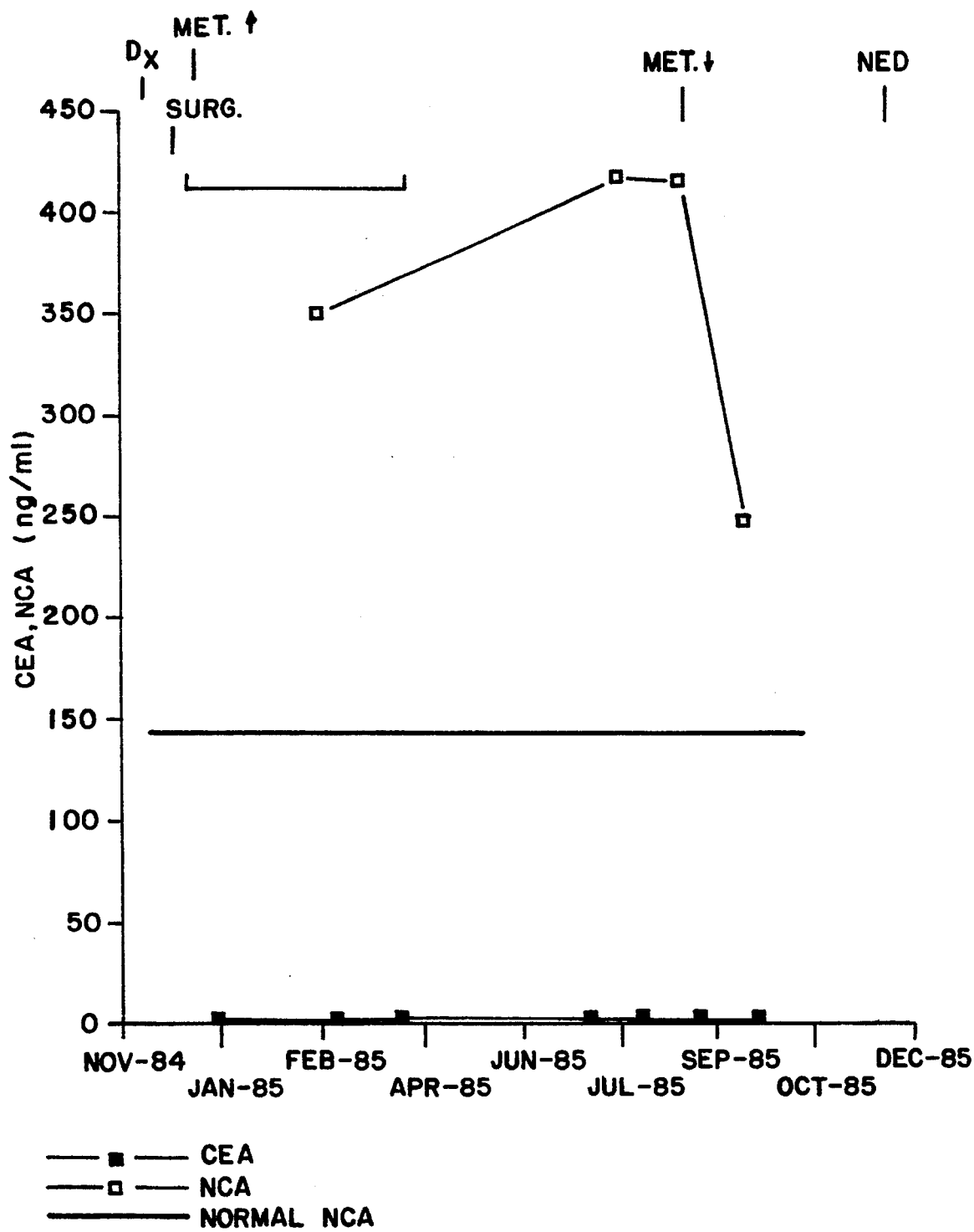
Figure 7:
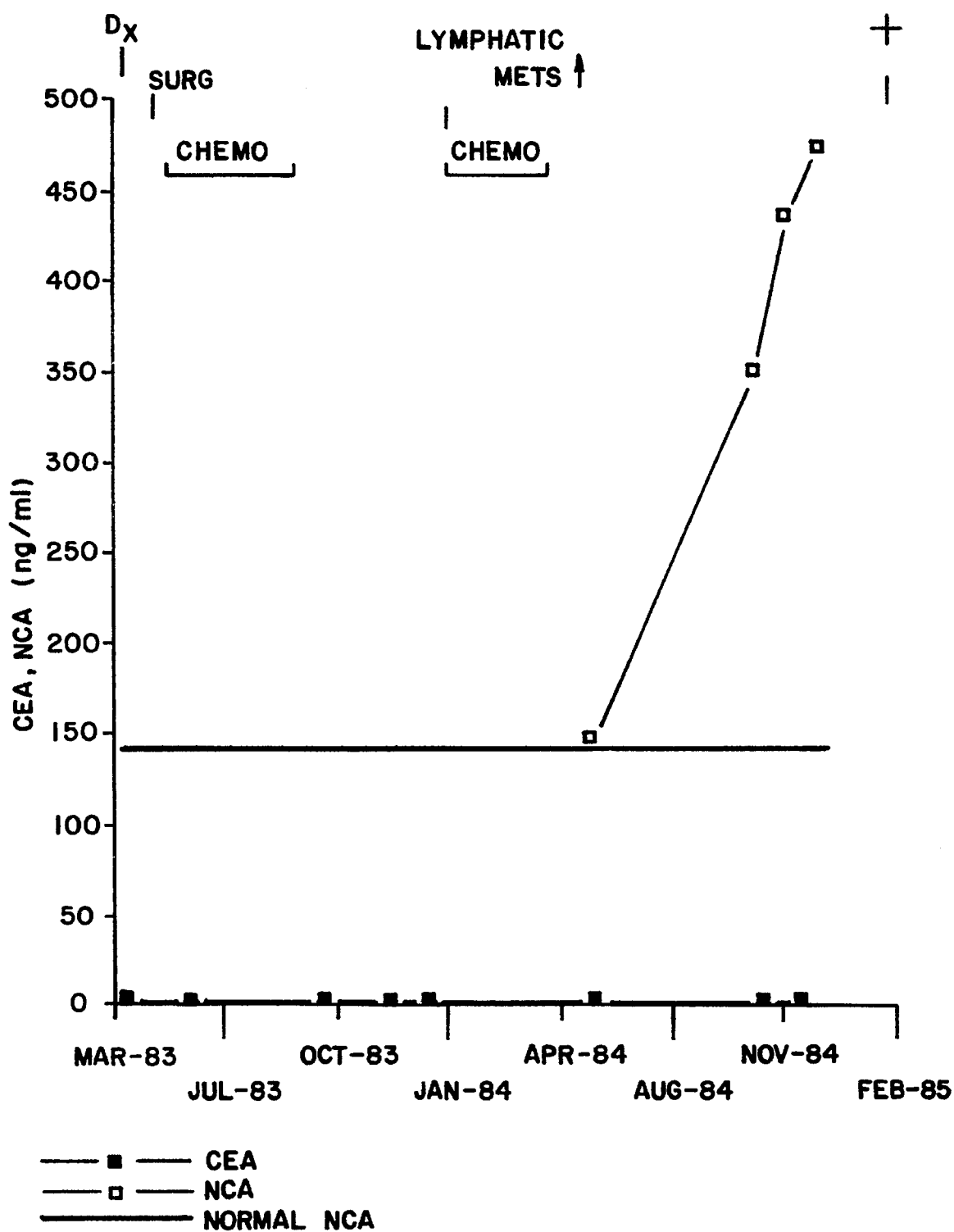
Figure 8:
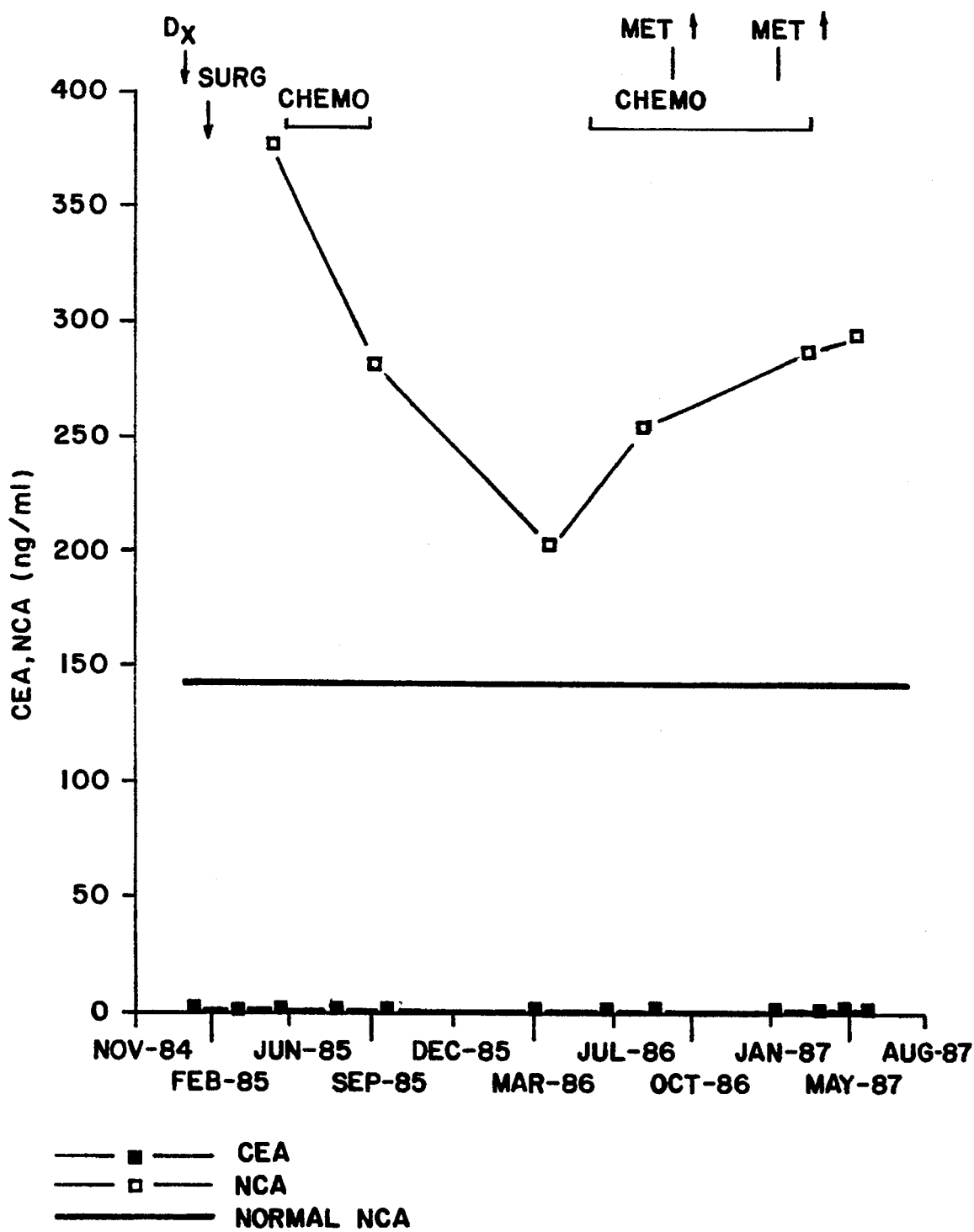

The antigenic specificity of the immunoassay for NCA 50/90 is established by the data shown in FIGS. 1 and 2. FIG. 1 shows the lack of cross-reactivity with CEA and with BGP. Testing with NCA 50/90 and NCA 95 purified from a recombinant expression vector containing cloned gene sequences (FIG. 2) shows that the assay is specific for NCA 50/90 (NCA-spleen is NCA purified from human spleen as described in von Kleist, S. et al, supra).

NCA 50/90 levels in the serum of clinically normal females were determined and the cutoff (95 h percentile confidence level) found to be 143 ng/ml (Table 1 ). The mean serum concentration of 202 clinically diagnosed breast cancer patients was 358 ng/ml.

TABLE 1

| Normals | Mean | 95th %ile |
| --- | --- | --- |
| Female nonsmokers (n = 50) | 64.9 ng/ml | 135 ng/ml |
| Female smokers (n = 25) | 82.3 ng/ml | 161 ng/ml |
| Total Females (n = 75) | 70.1 ng/ml | 143 ng/ml |
| Breast Cancer Patients | | |
| Percent showing elevated NCA 50/90 levels = 66% | 358.1 ng/ml (p < 0.0001) | 1756 ng/ml |

Changes in the serum levels of NCA 50/90 were found to correlate with the stage of disease in a significant number of patients diagnosed and under treatment for breast cancer. Serial serum samples were obtained from clinically confirmed breast cancer patients. These serial samples had a mean value of 209 ng/ml of NCA 50/90. Six examples of the correlation of serum CEA and NCA 50/90 levels and the clinical status of these patients are shown in FIGS. 3–8.

The graphs each show:
(a) the levels of NCA 50/90 as measured by the above-described sandwich immunoassay method,
(b) the levels of serum CEA that had been measured in a clinical laboratory and shown on the patient's chart,
(c) the 95th percentile cut-off value for normal NCA 50/90 (i.e., 143 ng/ml), and
(d) across the top of the graph, a summary of the disease progression using the following abbreviations:

"DX"=clinical diagnosis,

"Surg"=surgical procedure to remove the cancer,

"Chemo"=period during which chemotherapy was administered,

"Stable" an assessment by the attending physical that the patient's breast cancer has stabilized, "Met↑"=an assessment by the attending physician that metastasis had occurred or that the breast cancer was otherwise progressing, "Prog"=an assessment by the attending physician that the breast cancer was progressing, "†"=death of the patient, "Met↓"=an assessment by the attending physician that metastasis had been arrested, and "NED"=an assessment by the attending physician that there was no longer any evidence of disease.

In these examples, not only does serum NCA 50/90 show correlation with the clinical regression, stability, and progression of the disease, but also such correlation is more significant than the correlation with serum CEA levels (a commonly used serum marker for monitoring breast cancer).

The high incidence of elevated NCA 50/90 levels in breast cancer sera, and the significant correlation of clinical status with changes in the NCA 50/90 levels shows that the present method is useful as a means for monitoring the progression of breast cancer in patients.

Study 2

MAb 228.2—Monoclonal Antibody 228.2 specifically recognizes NCA 50/90, and was purified from mouse ascites fluids exactly as described for Study 1.

Biotinylation of Goat Antibody to CEA—An affinity purified polyclonal goat antiserum raised to CEA was purchased from BiosPacific, Emeryville, Calif., USA (Lot No. 015-B4302) and placed into 1.3 ml of 0.1M NaHCO$_3$, pH 8.5 at a concentration of 1.0 mg/ml. To this was added 18.5 µl of a 10 mg/ml solution of NHS-LC-biotin (Pierce, Rockford, Ill. USA, Catalog No. 21335) in deionized water to give a 50/1 molar excess of biotin to antibody. After incubation at 0° C. for 4 hours the biotinylated antibody was passed over a buffer-exchange column using 10 mM phosphate, pH 7.4/150 mM NaCl and stored at 4° C. with 0.1% thimerosal as preservative.

NCA 50/90 Calibrator—A cDNA corresponding to NCA 50/90 was derived from the breast tumor cell line BT-20 as described previously (Barnett, T., Goebel, S. J., Nothdurft, M. A. and J. J. Elting (1988) Genomics 3, 59–66). The coding region for the NCA 50/90 gene was modified by the elimination of the C-terminal hydrophobic region which signals replacement by a phosphoinositol glycan linkage, and the addition of a stretch of six histidine residues, also at the carboxyl terminus of the molecule (Drake, L. and Barnett, T. (1992) Biotechniques 12, 645–649). This construct was cloned into pVL1393 by PCR and expressed using recombinant baculovirus phage to infect Spodoptera frugiperda (Sf9) cells. NCA 50/90 was affinity purified from Sf9 supernatant fluids using a zinc-imidoacetate-Sepharose® column as described (Drake and Barnett, supra). The concentration of NCA 50/90 was determined by the BCA protein assay (Pierce, Cat. No. 23225G). For use as a calibrator in the NCA 50/90 ELISA, purified recombinant NCA 50/90 was diluted in TBST/5 % BSA as described below.

NCA 50/90-Specific Immunoassay—A sandwich ELISA was configured using the 228.2 monoclonal antibody as the solid phase capture antibody, and the biotinylated polyclonal anti-CEA as the reporter antibody. 96-well ELISA plates (Iratoulon IV, Dynatech Laboratories, Chantilly, Va., USA) were coated with 100 µl of 228.2 antibody at 5 µg/ml in 0.1M NaHCO$_3$, pH 9.0 and incubated overnight at 4° C. Wells were emptied and unreacted sites on the plates were quenched by the addition of 200 µl of 20 mM Tris, pH 7.5/150 mM NaCl/0.05% Tween 20 (TBST) with 5% bovine albumin (BSA, fraction V, Sigma Chemical Company, St. Louis, Mo., USA), Catalog No. A-7030) followed by a 1 hour incubation at 37° C. Wells were washed 6 times with TBST, and 25 µl of either NCA 50/90 calibrators diluted in TBST/5% BSA or 25 µl of patient sample was added. An equal volume of 50 mM HEPES, pH 7.0/500 mM NaCl/200 µg/ml mouse IgG/5% BSA/50 µg/ml gentamycin/0.1% (w/v) NaN$_3$ (sample diluent) was added to each well and the plates were incubated for 2 hours at 37° C. After washing 6 times, a 100 µl volume of a 0.3 µg/ml solution of goat anti-CEA-biotin in 50 mM HEPES, pH 7.0/150 mM NaCl/1 mM MgCl$_2$.6H$_2$O/0.1 mM ZnCl$_2$/5 % BSA/50/µg/ml gentamycin/0.1% NaN$_3$ (conjugate diluent) was added to all wells and incubated for 1 hour at 37° C. The wells were washed a further 6 times, and 100 µl of streptavidin conjugated to alkaline phosphatase (Pierce, Catalog No. 21324G) diluted 1/5000 in conjugate diluent was added. After a 1 hour incubation at 37° C., the plates were washed 12 times with TBST and incubated with 100 µl of p-nitrophenyl phosphate in DEA substrate buffer (Pierce, Catalog No. 34064) for 30 minutes. The reaction was stopped with 100 µl N NaOH and absorbance at 405 nm minus absorbance at 490 nm determined using a microplate reader (Thermo-Max, Molecular Devices Corp., Menlo Park, Calif., USA). The amount of NCA 50/90 was determined for each test sample by comparison with the calibrator standard curve.

Patient Samples—Serum was prepared from blood drawn from normal healthy volunteers by Hudson Valley Blood Services of Valhalla, N.Y., USA. Samples from patients with inactive or active breast cancer were obtained from Dianon Systems of Stratford, Conn., USA, and from M. D. Anderson Cancer Center, Houston, Tex., USA. Patient disease status was determined from information supplied by attending physicians as well as results of testing for the tumor markers CEA, lipid associated sialic acid (LASA), and CA 15-3.

Results

Figure 9:
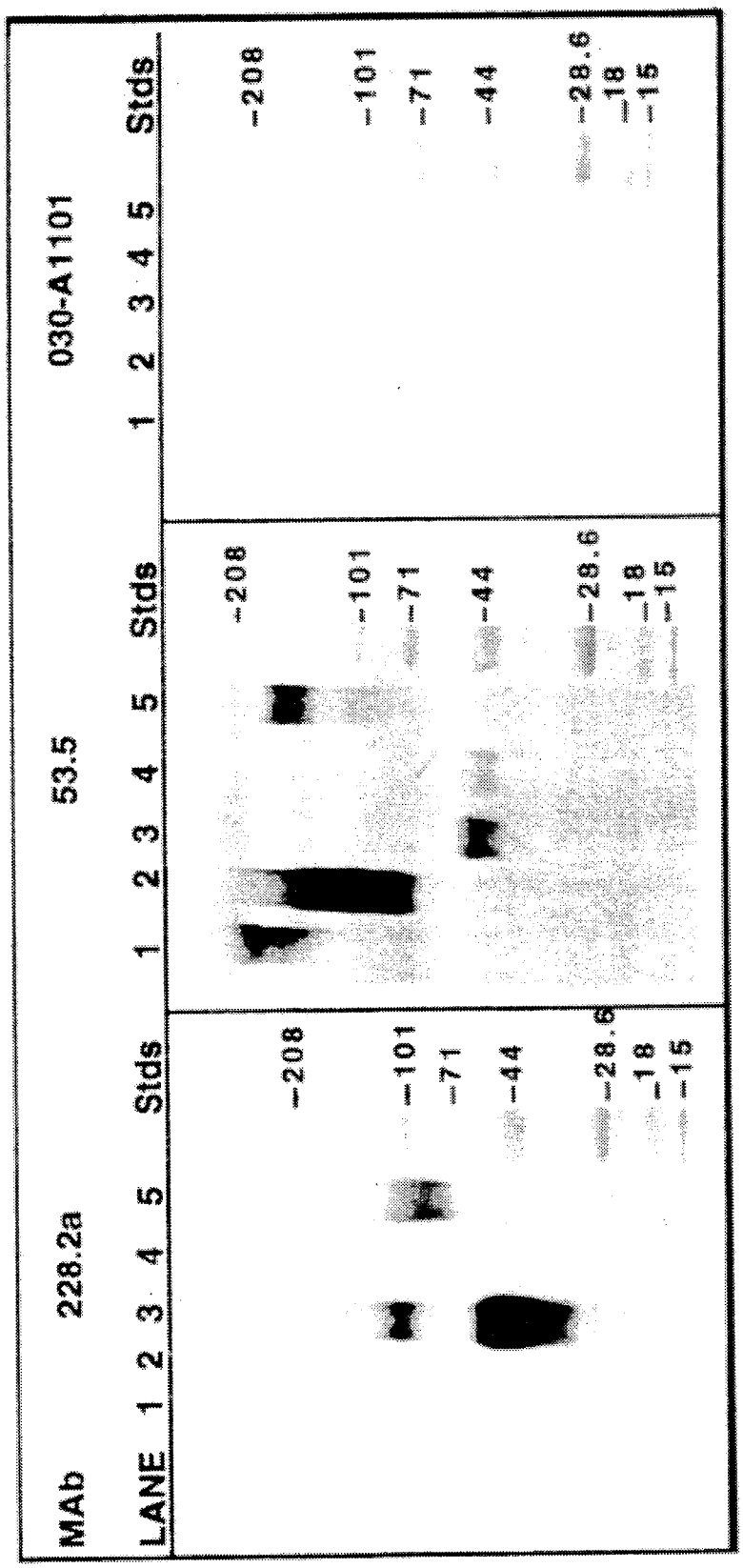
FIG. 9 is a reproduction of a Western blot showing that the 228.2 monoclonal antibody binds to NCA 50/90, but does not recognize NCA 95, CEA, BGPs or NCA 2. For each of the three blots presented, the indicated monoclonal antibodies were blotted against CEA family members as follows: lane 1, CEA; lane 2, BGP; lane 3, NCA 50/90; lane 4, NCA 95; lane 5, NCA 2. The control blots in this figure also show that the preparation of NCA 50/90 used as a standard in the NCA 50/90 ELISA contains only NCA 50/90.

The antigenic specificity of the 228.2 monoclonal antibody was determined first by Western blotting and results are shown in FIG. 9. The 228.2 MAb reacts specifically with NCA 50/90 and not with other proteins related to CEA. The reactivity of the 228.2 MAb with the high molecular weight band of Mr 110,000 in lane 3 of the 228.2a blot, probably represents the formation of SDS-stable protein dimers. Because NCA 2 is a fragment of CEA and the 228.2 antibody does not bid to CEA, it would be expected that the 228.2 MAb would not recognize NCA 2. Results in FIG. 1 show that this is indeed the case. The reactivity of the 228.2 MAb with the NCA 2 preparation is with an M$_r$ 90,000 protein which does not comigrate with the M$_r$ 160,000 NCA 2 protein, and is likely to represent a low level of contamination of the NCA 2 preparation with the M$_r$ 90,000 form of NCA 50/90. The reactivity of the positive control MAb 53.5 with each of the antigen preparations demonstrates the presence of the relevant glycoproteins in each preparation. In addition, the 53.5 MAb reacted only with a protein of M$_r$ 50,000 in the NCA 50/90 preparation, which demonstrates the antigenic purity of the NCA 50/90 preparation. The MAb 030-A1101 binds to alpha fetoprotein and was used as negative control.

Figure 10:
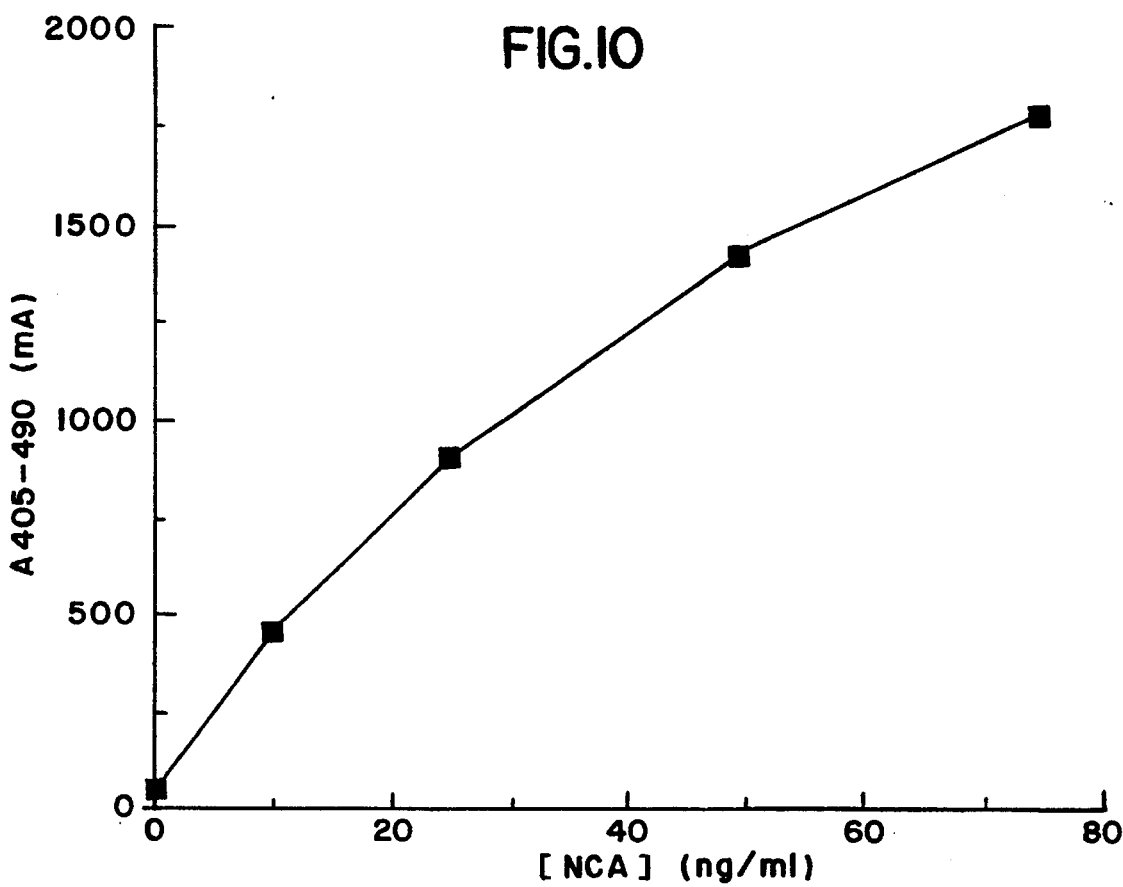
FIG. 10 is a graph showing the standard curve obtained in the NCA 50/90 ELISA.
Figure 11:
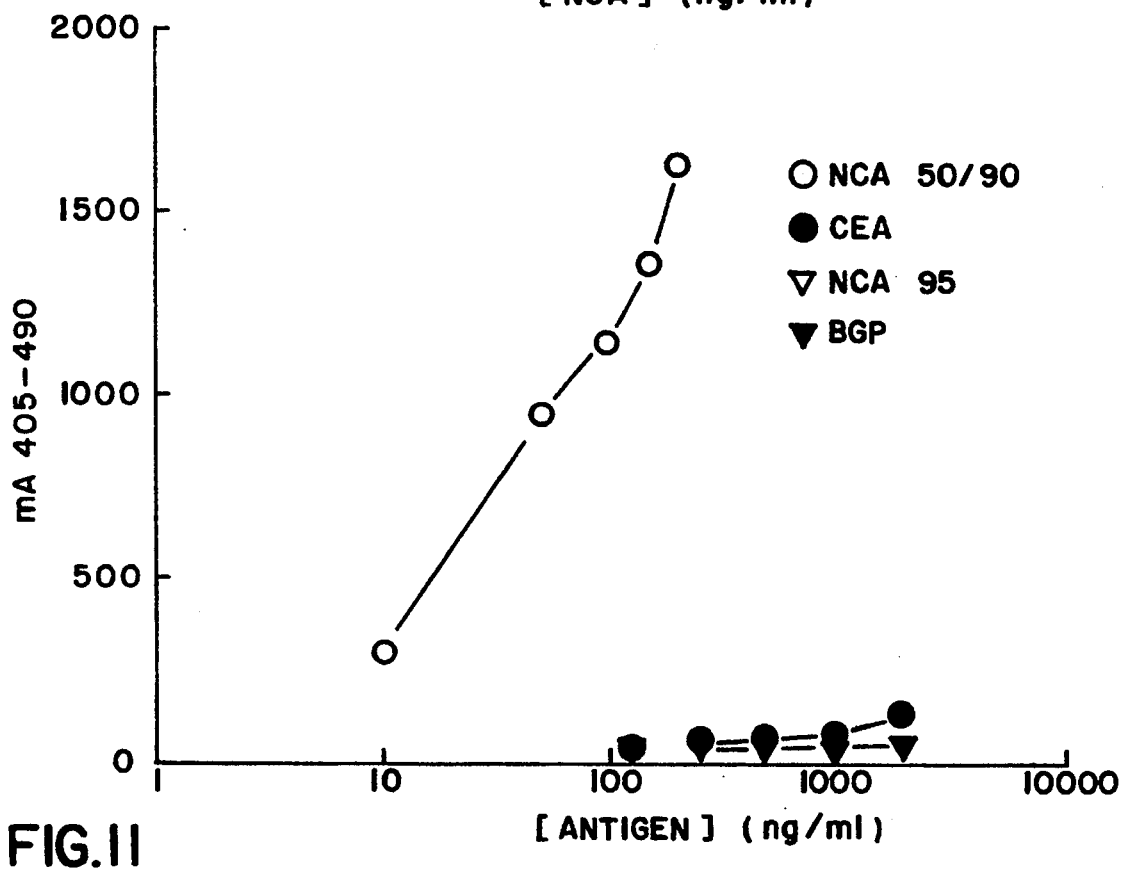
FIG. 11 is a graph showing that the NCA 50/90 ELISA has no significant cross reactivity with CEA, NCA 95 or BGP.
Figure 12:
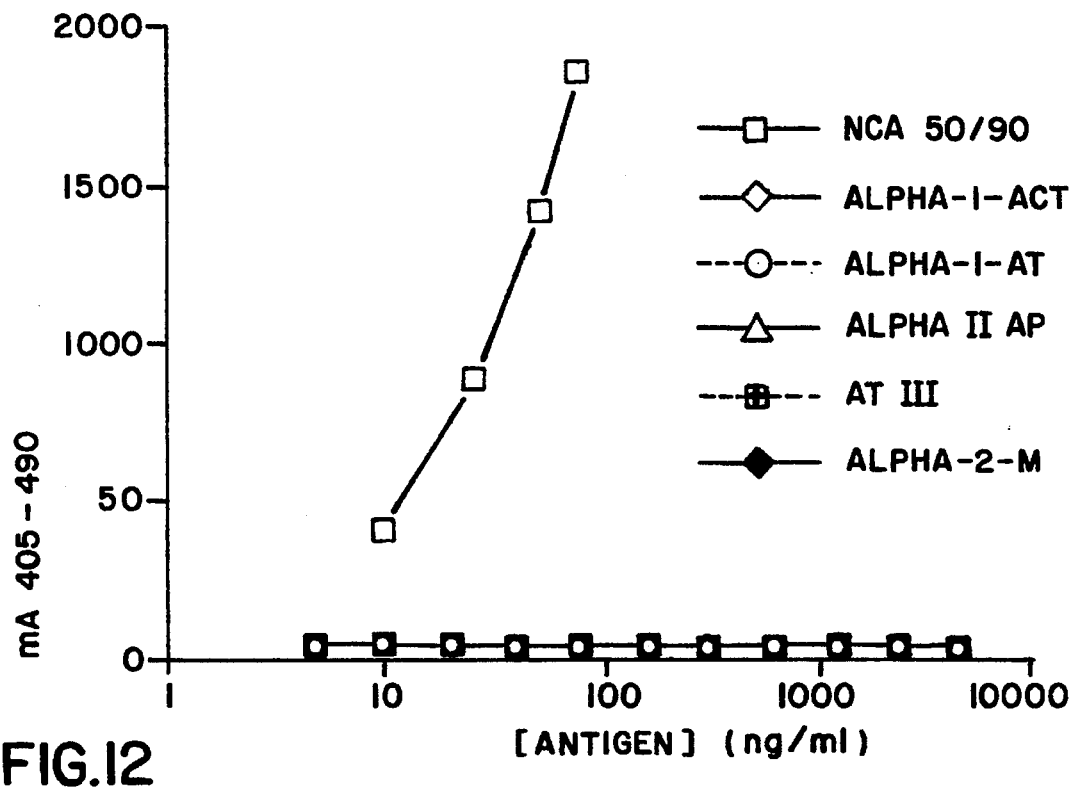
FIG. 12 is a graph showing that the NCA 50/90 ELISA has no significant cross reactivity with $\alpha$-1-antichymotrypsin, $\alpha$-1-antitrypsin, $\alpha$-2-macroglobuln, $\alpha$-2-antiplasmin and antithrombin III.

The standard curve presented in FIG. 10 demonstrates a nonlinear increase in absorbance as a function of NCA 50/90 concentration. A nonlinear spline curve fit program was used to convert raw patient data to NCA 50/90 concentrations. The data in FIGS. 11 and 12 demonstrate that the NCA 50/90 ELISA shows no significant reactivity with CEA, NCA 95, BGPs, α-1-antichymotrypsin, α-1-antitrypsin, α-2-macroglobulin, α-2-antiplasmin and antithrombin III. The potential for cross reactivity with serine proteinase inhibitors stems from observations that biochemically purified CEA and NCA may associate with molecules with amino acid homology to α-1-antichymotrypsin and α-1-antitrypsin (Orjaseter, H. (1976) Acta Path. Microbiol. Scand. 84, 235–244; and Grunert, F., Abuharfeil, N., Luckenbach, G. A. and S. von Kleist (1984) Tumor Biol. 5, 221–232). Since the MAb 228.2 was raised to biochemically purified NCA 50/90 from spleen, there is also potential for cross reactivity with related proteins.

Figure 13:
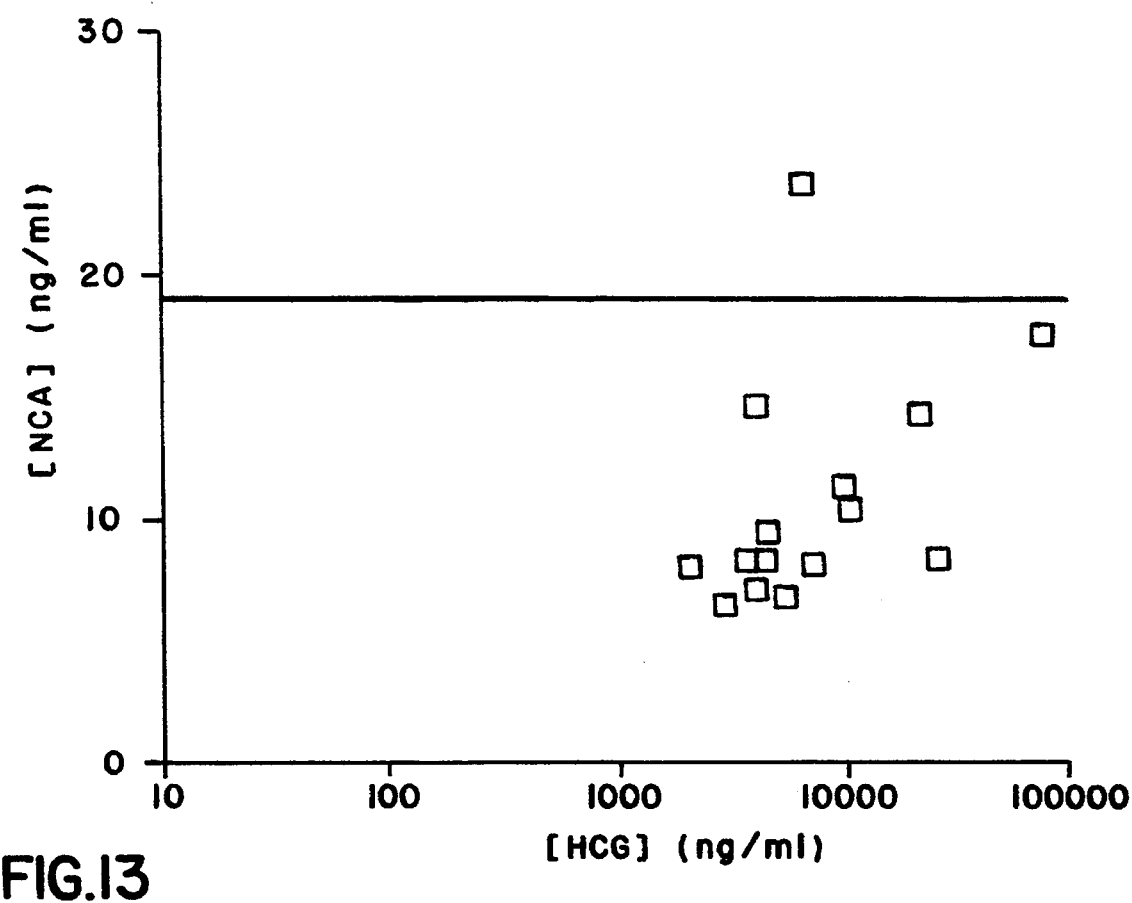
FIG. 13 is a graph showing that the NCA 50/90 ELISA has no significant reactivity with serum from pregnant women which demonstrates a lack of reactivity with PSG.

An additional member of the CEA gene family is pregnancy specific β-glycoprotein (PSG) which is elevated in the serum of pregnant women. Reactivity to this protein was tested by examining sera from 15 pregnant women with HCG values ranging from 2,200 to 79,000 (normal cutoff for HCG=10). As can be seen in FIG. 13, only one patient showed an NCA 50/90 value above the cutoff value of 18 ng/ml (as determined below), which demonstrates that the NCA 50/90 ELISA does not detect PSG.

Figure 14:
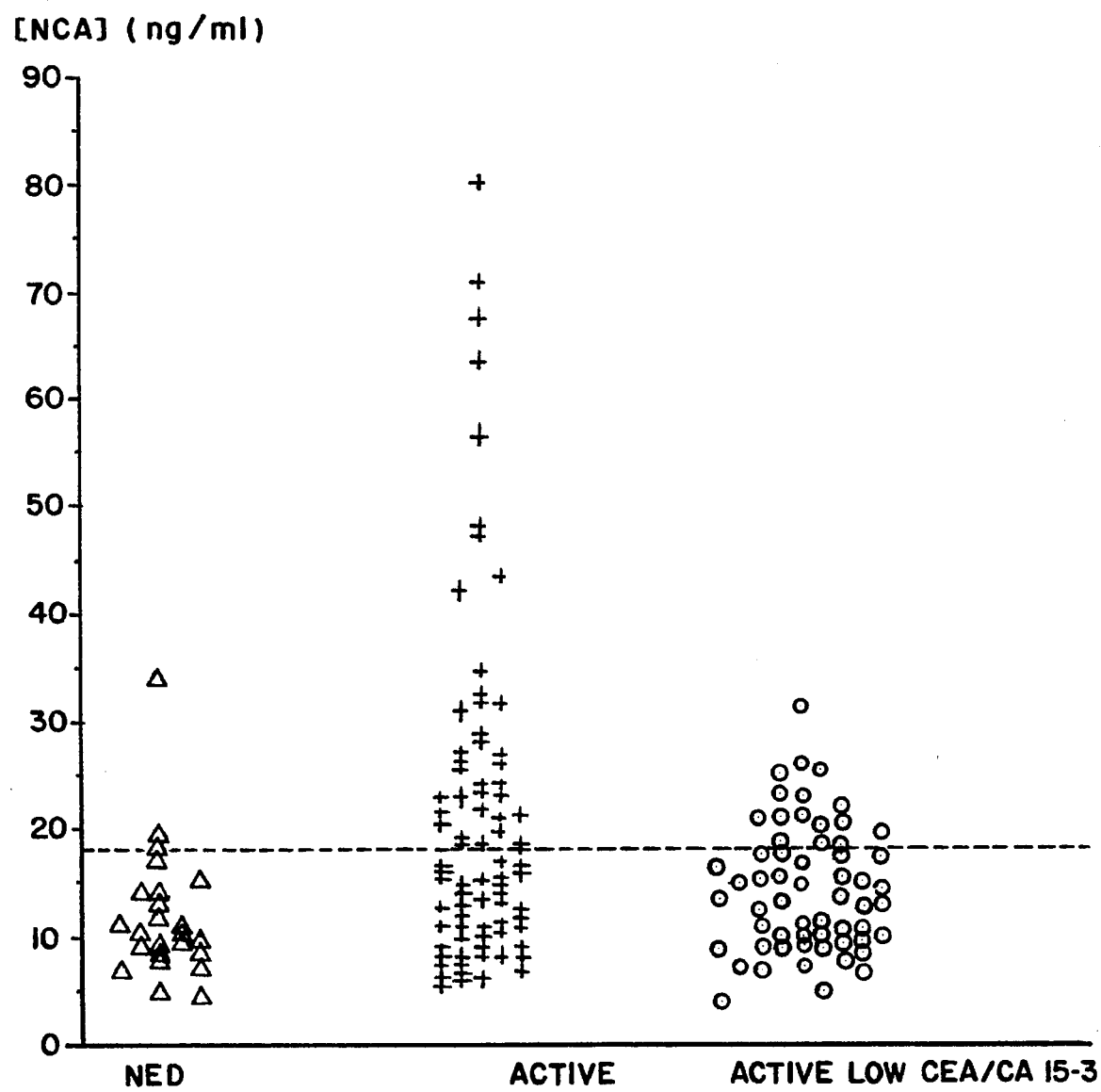
FIG. 14 is a graph which demonstrates that the level of NCA 50/90 is elevated in the serum of patients with breast cancer.

To establish a cutoff value for normal blood levels of NCA 50/90, the level of NCA 50/90 was measured in serum from 92 normal healthy volunteers. A 95% cutoff value was determined to be 18 ng/ml. This cutoff value differs from that for Study 1 due to differences in calibrator material. NCA 50/90 values were then measured in plasma from 31 breast cancer patients undergoing treatment who were clinically free of cancer, and it was found that 3/31 of the values were above the cutoff value (FIG. 14). In contrast, 42% of samples from 113 patients with active breast cancer were above the cutoff value, which demonstrates that NCA 50/90 is elevated above normal levels in the blood of some patients with breast cancer.

Plasma from 26 breast cancer patients who had active cancer by clinical examination, but whose levels of CEA and CA 15-3 were below cutoff for those markers (5 ng/ml and 35 ng/ml, respectively) was also tested. Of 26 such patients, 7 had NCA 50/90 values in excess of 18 ng/ml (27%). These results indicate that NCA 50/90 values can be used to manage patients whose clinical status cannot be monitored by changes in currently available biomarkers.

Figure 15:
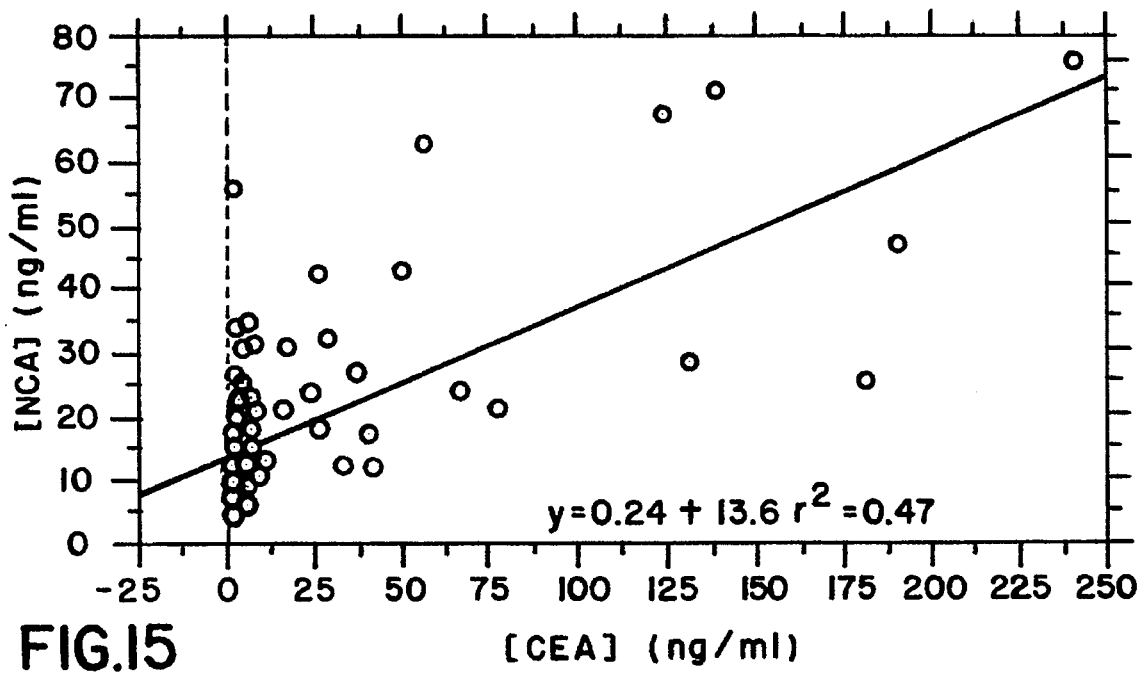
FIG. 15 is a graph which shows a lack of correlation between blood levels of CEA and NCA 50/90 in patients under treatment for breast cancer.
Figure 16:
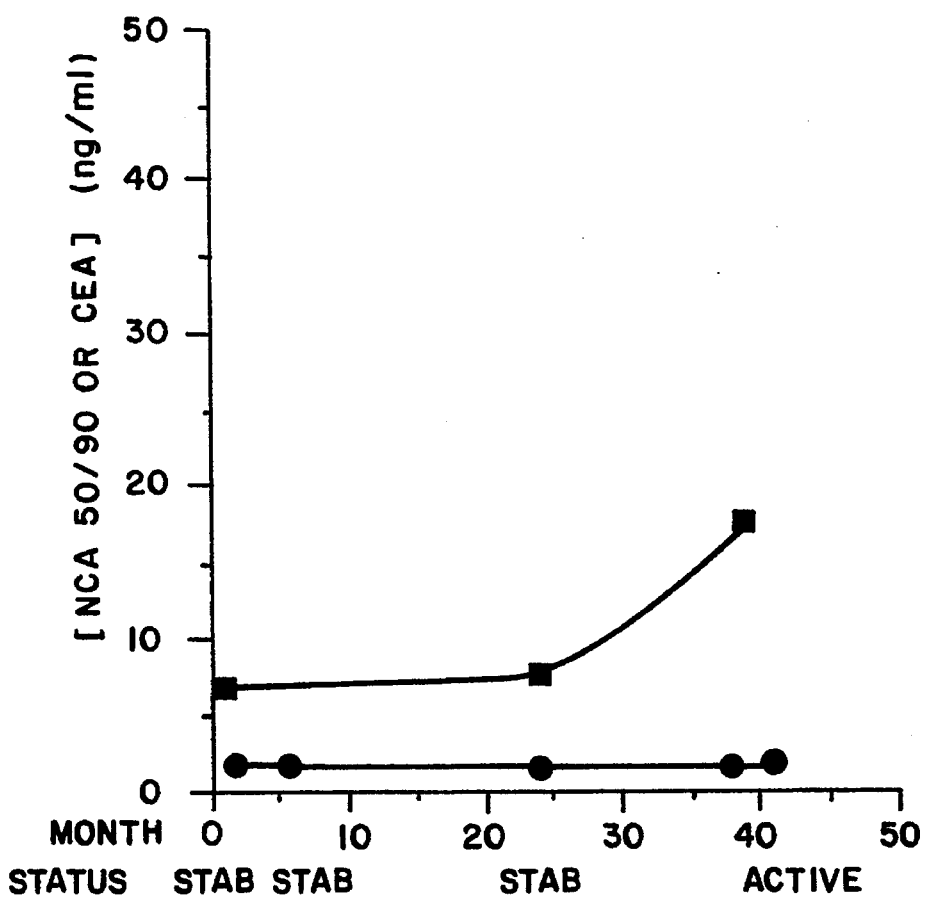
FIGS. 16–20 are a series of graphs which illustrate NCA 50/90 levels in longitudinal serum samples of individual patients with breast cancer.
Figure 17:
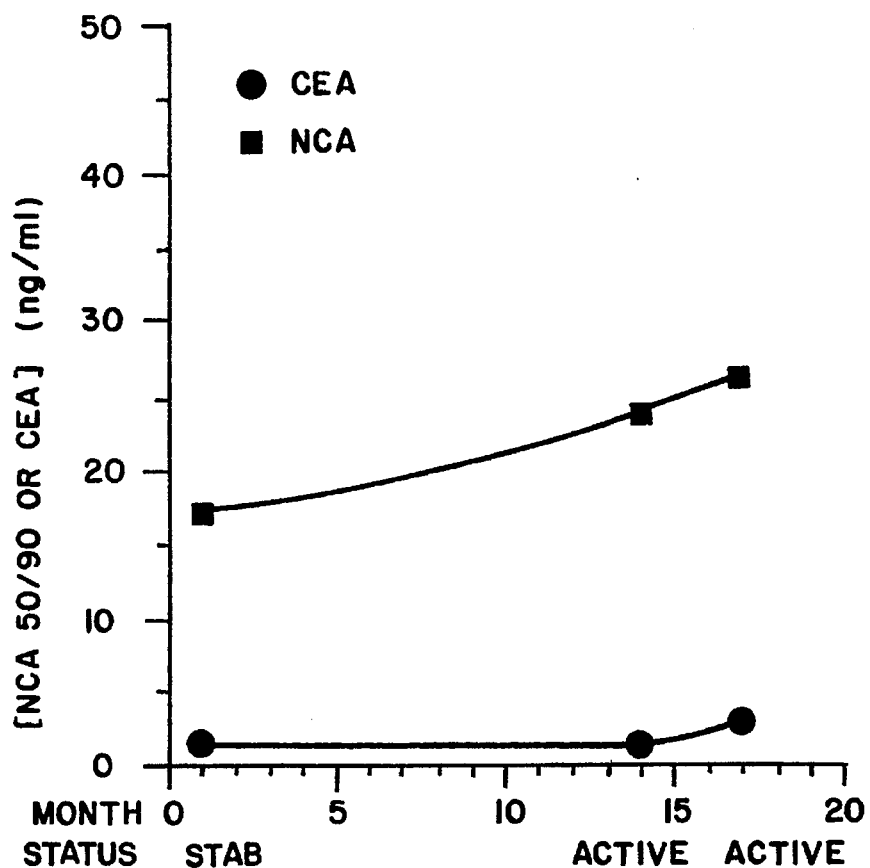
Figure 18:
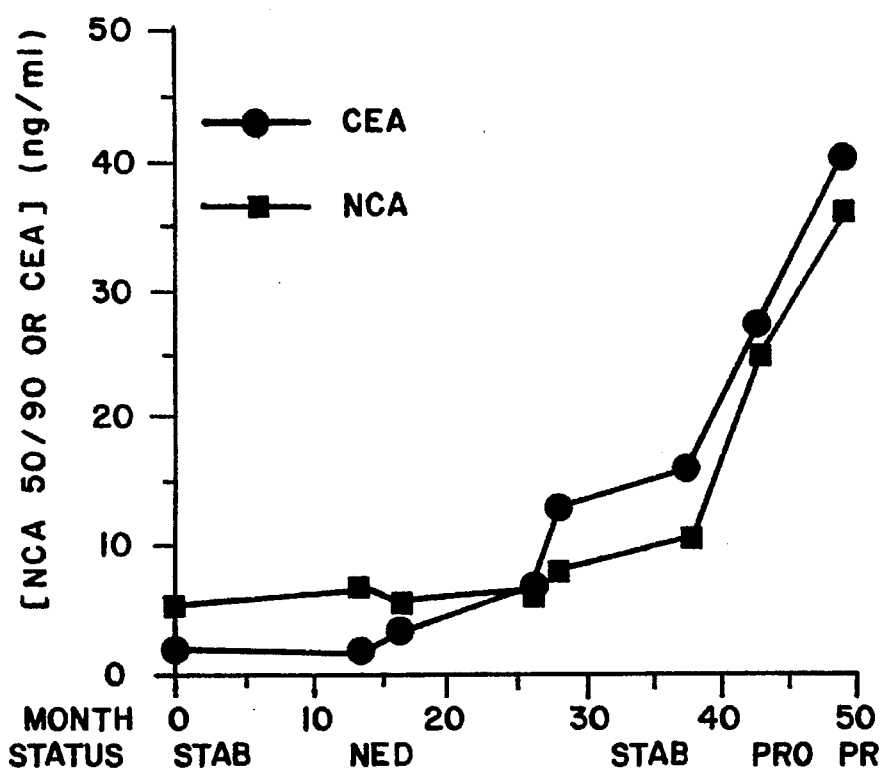
Figure 19:
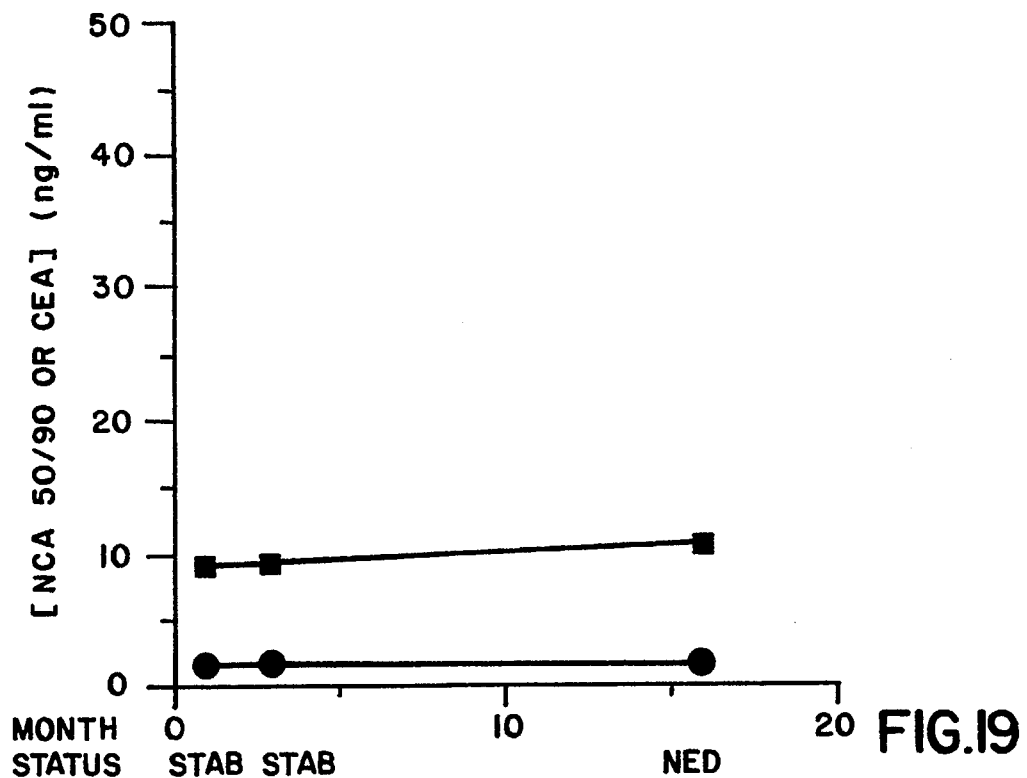
Figure 20:
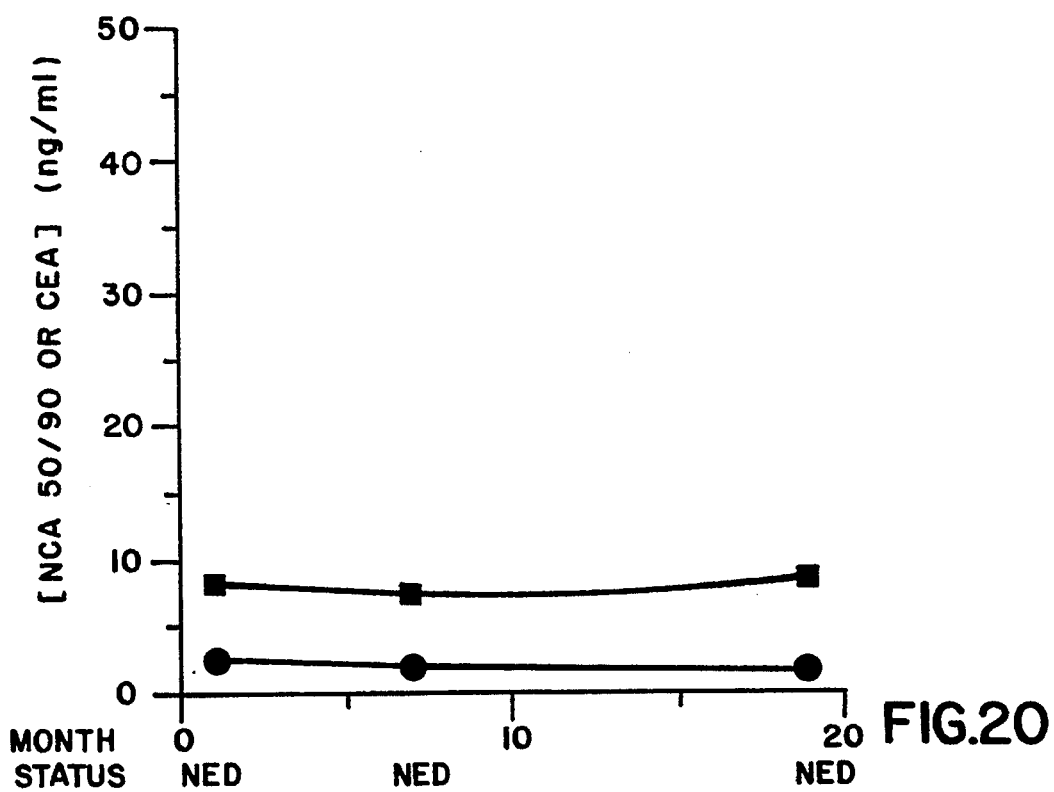

Because NCA 50/90 and CEA are both overexpressed in some tumor tissues, it may be expected that elevations of NCA 50/90 in the blood of cancer patients would correlate with increases in CEA values. To test this, we compared the values for NCA 50/90 and CEA in 143 patients under treatment for breast cancer. The results in FIG. 15 demonstrate that the levels of NCA 50/90 and CEA are correlated only poorly (correlation coefficient, $r^2$=0.47). This was unexpected and demonstrates that increases in blood levels of NCA 50/90 will occur in a population of cancer patients which is different from that with increases in blood levels of CEA. This again indicates that measurement of NCA 50/90 in blood can be of additional clinical value to currently used biomarkers.

The serum level of NCA 50/90 was found to correlate with the status of disease in 20 patients diagnosed with and under treatment for breast cancer. Results obtained with samples from 5 of these patients are presented in FIGS. 16–20. Patient BS6 had inactive cancer in the early stages of the study, but developed recurrent disease at later time points. NCA 50/90 showed elevated values when the clinical condition worsened from stable (STAB) to progressive disease (PRO), as determined by the attending physician. Results with Patients BS3 and BS5 remained below cutoff for both NCA 50/90 and CEA throughout the course of the study which is in agreement with the clinical condition of these patients. Results with Patients BS1 and BS19 showed that NCA 50/90 detected cancer recurrence in these patients, whereas CEA values remained below cutoff. These results again indicate that NCA 50/90 can be of additional value to current biomarkers in the management of breast cancer patients. The combined results with all 20 patients demonstrate that NCA 50/90 values correctly reflected disease status in 88% of the longitudinal samples. Taken together, these results demonstrate that NCA 50/90 can be used to monitor disease status in breast cancer patients under treatment.

The present invention has been particularly described and exemplified above. Clearly, many other variations and modifications of the invention can be made without departing from the spirit and scope hereof.

What is claimed is:

1. A method for aiding in the diagnosis of breast cancer in a patient, comprising the steps of determining the amount of NCA 50/90 in a blood sample obtained from said patient and comparing said measured amount of NCA 50/90 to the mean amount of NCA 50/90 in the normal population, whereby the presence of a significantly increased higher amount of NCA 50/90 in the patient's blood is an indication of breast cancer in the patient.

2. The method of claim 1 wherein the amount of NCA 50/90 in the patient's blood sample is measured by performing a sandwich immunoassay in which at least one of the antibody reagents is specific for NCA 50/90 with no substantial reactivity for CEA, NCA 95 or BGP.

3. The method of claim 2 wherein said NCA 50/90 specific antibody reagent is a monoclonal antibody reagent.

4. The method of claim 2 wherein said NCA 50/90 specific antibody reagent is the monoclonal antibody produced by the hybridoma deposited with the American Type Culture Collection and identified as ATCC HB11204, or a monoclonal antibody which binds to the same epitope as the aforesaid monoclonal antibody produced by hybridoma ATCC11204.

5. The method of claim 1 wherein said blood samples is a serum or plasma sample.

6. A method for monitoring the progression of breast cancer in a patient, comprising performing a series of specific immunoassays over time to determine changes in the level of NCA 50/90 in blood samples obtained from such patient, whereby increases in blood NCA 50/90 levels indicate a deteriorating condition while decreases in blood NCA 50/90 levels indicate an improving condition.

7. The method of claim 6 wherein the immunoassays performed are sandwich immunoassays in which at least one of the antibody reagents is specific for NCA 50/90 with no substantial reactivity for CEA, NCA 95, BGP or PSG.

8. The method of claim 7 wherein said NCA 50/90 specific antibody reagent is a monoclonal antibody reagent.

9. The method of claim 7 wherein said NCA 50/90 specific antibody reagent is the monoclonal antibody produced by the hybridoma deposited with the American Type Culture Collection and identified as ATCC HB11204, or a monoclonal antibody which binds to the same epitope as the aforesaid monoclonal antibody produced by hybridoma ATCC11204.

10. The method of claim 6 wherein said blood samples are serum or plasma samples.

11. An NCA 50/90 specific antibody reagent comprising the monoclonal antibody produced by the hybridoma deposited with the American Type Culture Collection and identified as ATCC HB11204, or a monoclonal antibody which binds to the same epitope as the aforesaid monoclonal antibody produced by hybridoma ATCC11204.

12. A sandwich immunoassay test kit for use in the determination of NCA 50/90 in a blood sample, comprising, as first antibody reagent, the antibody reagent of claim 11, and a second antibody reagent capable of binding specifically or nonspecifically with NCA 50/90.

13. The test kit of claim 12 wherein said second antibody reagent is also monoclonal.

14. The test kit of claim 12 wherein one of said antibody reagents is labeled with an enzyme.

* * * * *